US006187306B1

(12) United States Patent
Pardoll et al.

(10) Patent No.: US 6,187,306 B1
(45) Date of Patent: Feb. 13, 2001

(54) MELANOMA CELL LINES EXPRESSING SHARED IMMUNODOMINANT MELANOMA ANTIGENS AND METHODS OF USING SAME

(75) Inventors: Drew M. Pardoll, Brookeville; Elizabeth Jaffee, Lutherville; Adam Adler, Pikesville; Suzanne L. Topalian, Brookeville; Steven A. Rosenberg, Potomac, all of MD (US)

(73) Assignees: The Johns Hopkins Universtiy, Baltimore, MD (US); The United States of America as represented by the Department of Health and Human Services, Washington, DC (US)

( * ) Notice: Under 35 U.S.C. 154(b), the term of this patent shall be extended for 0 days.

(21) Appl. No.: 08/906,029

(22) Filed: Aug. 5, 1997

Related U.S. Application Data

(60) Provisional application No. 60/024,098, filed on Aug. 16, 1996.

(51) Int. Cl.[7] .............................. A61K 48/00; C12N 15/85

(52) U.S. Cl. ................. 424/93.21; 424/93.2; 424/277.1; 435/325; 435/455; 514/44

(58) Field of Search .................................. 435/325, 455; 536/23.1, 23.5; 424/93.1; 530/395, 351, 350

(56) References Cited

U.S. PATENT DOCUMENTS

| | | |
|---|---|---|
| 4,595,653 | 6/1986 | Kronenberg . |
| 5,342,774 | 8/1994 | Boon et al. . |
| 5,399,346 | 3/1995 | Anderson et al. . |
| 5,637,483 | * 6/1997 | Dranoff et al. .................. 424/93.21 |

FOREIGN PATENT DOCUMENTS

| | | |
|---|---|---|
| 0668 350 | 8/1995 | (EP) . |
| WO 90/11085 | 10/1990 | (WO) . |
| WO 92/05262 | 4/1992 | (WO) . |
| WO 9306867 | 4/1993 | (WO) . |
| WO 95/31107 | * 11/1995 | (WO) ............................ A01N/63/00 |

OTHER PUBLICATIONS

Mulligan, R. The basic science of gene therapy. Science. vol. 260, p. 926–932, May 14, 1993.*
Maeurer, M.J., et al. New treatment options for patient with melanoma: review of melanoma–derived T–cell epitope–based peptide vaccines. Melanoma Research, vol. 6 pages 11–24, Feb. 1996.*
Belli, F. Active immunization of metastatic melanoma patients with interleukin–2–ransduced allogeneic melanoma cells: evaluation of efficacy and tolerability. Cancer immunology, immunotherapy, vol. 44, pp. 197–203, Jun. 1997.*
Dalemans, W. From in vitro to in vivo. Progress in the use of cultured cells for human therapy. Cytotechnology, vol. 16, pp. 189–194, 1994.*

Topalian, S.L. et al. Human CD4+ T cells specifically recognize a shared melanoma–associated antigen encoded by the tyrosinase gene. Proc. Natl. Acad. Sci., USA, vol. 91, pp. 9496–9465, Sep. 1994.*
Hoon, DSB et al. Supressor cell activity in a randomized trial of patients receiving active specific immunotherapy with melanoma cell vaccine and low dosage of cyclophosphamide. Cnacer research, vol. 50, pp. 5358–5364, Sep. 1, 1990.*
Viewing, et al., Cancer Investigation, vol. 13, pp. 193–201, 1995.*
Dranoff et al. Proc. Natl. Acad. Sci. USA, vol. 90, pp. 3539–3543, 1993.*
Adler et al. Journal of Immunotherapy, vol. 13, p. 55, 1993.*
Leong et al. Cancer Immunol. Immunother., vol. 40, pp. 397–409, 1995.*
Dranoff et al., *Proc. Natl. Acad. Sci. USA*, 90, 3539–3543 (1993).
Topalian et al., *Proc. Natl. Acad. Sci. USA*, 91, 9461–9465 (1994).
Rosenberg, Proceedings of the American Association for Cancer Research 37, 642–643 (1996).
Darrow et al., *J. Immunol.*, 142, 3329–3335 (1989).
Gastl et al., *Cancer Reseach*, 52, 6229–6236 (1992).
Golumbek et al., *Cancer Research*, 53, 5841–5844 (1993).
Hom et al., *J. Immunother.*, 10, 153–164 (1991).
Huang et al., *Science*, 264, 961–965 (1994).
Jaffee et al., Seminars in Oncology, 22, 81–91 (1995).
Kawakami et al., *J. Immunol.*, 148, 638–643 (1992).
Szuromi (ed.), *Science*, 264, 885 (1994).
Database WPI, Week 7808, Derwent Info. Ltd., AN 77–09702Y/06 (JP 53–003–509 abstract), Jan. 13, 1978.
Database WPI, Week 8928, Derwent Info. Ltd., AN 89–206442/28 (WO 89/05631 abstract), Jun. 29, 1989.
Database WPI, Week 9035, Derwent Info. Ltd., AN 90–266194/35 (JP 2–188–532 abstract), Jul. 24, 1990.
Database WPI, Week 9250, Derwent Info. Ltd., AN 92–415476/50 (WO 92/20374 abstract), Nov. 6, 1992.
Database WPI, Week 9317, Derwent Info. Ltd., AN 93–136183/17 (EP 538,952 abstract), Apr. 28, 1998.

(List continued on next page.)

*Primary Examiner*—John L. LeGuyader
*Assistant Examiner*—Michael C. Wilson
(74) *Attorney, Agent, or Firm*—Shmuel Livnat; Rader Fishman & Grauer PLLC

(57) ABSTRACT

The invention pertains to a method of treating or protecting against melanoma that comprises (a) obtaining a melanoma cell line that expresses one or more shared immunodominant melanoma antigens, (b) modifying the melanoma cell line to render it capable of producing an increased level of a cytokine relative to the unmodified cell line, and (c) administering the melanoma cell line to a mammalian host that has melanoma or is at risk for developing melanoma. Preferably the melanoma cell line is allogeneic and is not MHC-matched to the host.

17 Claims, No Drawings

OTHER PUBLICATIONS

Database WPI, Weeks 9432 and 9518, Derwent Info. Ltd., AN 94–264105/32 (WO 94/17192 abstract) Aug. 4, 1994.

Database WPI, Week 9503, Derwent Info. Ltd., AN 95–022468/03 (WO 94/27635 abstract), Dec. 8, 1994.

Database WPI, Week 9536, Derwent Info. Ltd., AN 94–169430/21 (EP 599,077 abstract), Jun. 1, 1994.

* cited by examiner

MELANOMA CELL LINES EXPRESSING SHARED IMMUNODOMINANT MELANOMA ANTIGENS AND METHODS OF USING SAME

CROSS REFERENCE TO RELATED APPLICATIONS

The present application claims priority to U.S. Provisional Application Serial No. 60/024,098, filed Aug. 16, 1996.

TECHNICAL FIELD OF THE INVENTION

The present invention pertains to a method of treating or protecting against melanoma using as a vaccine one or more melanoma tumor cell lines that express multiple immunodominantshared melanoma antigens. In particular, the invention pertains to the method of using an allogeneic melanoma cell line as a vaccine. The present invention also relates to a melanoma cell line that expresses shared immunodominant melanoma antigens, and to a composition comprising cells of the melanoma cell line.

BACKGROUND OF THE INVENTION

It generally is accepted that tumor cells contain multiple specific alterations in the cellular genome responsible for their cancerous phenotype. These alterations affect the expression or function of genes that control cell growth and differentiation. For instance, typically these mutations are observed in oncogenes, or positive effectors of cellular transformation, such as ras, and in tumor suppressor genes (or recessive oncogenes) encoding negative growth regulators, the loss of function of which results in expression of a transformed phenotype. Such recessive oncogenes include p53, p21, Rb1, DCC, MCC, NFI, and WTI.

Immunotherapy is a potential therapeutic approach for the treatment of cancer. Immunotherapy is based on the premise that the failure of the immune system to reject spontaneously arising tumors is related to the failure of the immune system to appropriately respond to tumor antigens. In a functioning immune system, tumor antigens are processed and expressed on the cell surface in the context of major histocompatibility complex (MHC) class I and II molecules, which, in humans, also are termed "human leukocyte associated" (HLA) molecules. Complexes of MHC class I and II molecules with antigenic peptides are recognized by $CD8^+$ and $CD4^+$ T cells, respectively. This recognition generates a set of secondary cellular signals and the paracrine release of specific cytokines or soluble so-called "biological response modifiers", that mediate interactions between cells and stimulate host defenses to fight off disease. The release of cytokines then results in the proliferation of antigen-specific T cells.

Thus, active immunotherapy involves the injection of tumor cells to generate either a novel or an enhanced systemic immune response. The ability of this immunotherapeutic approach to augment a systemic T cell response against a tumor has been previously disclosed, e.g., amongst others, see International Application WO 92/05262, Fearon et al., Cell, 60, 397–403 (1990), and Dranoff et al., Proc. Natl. Acad. Sci., 90, 3539–43 (1993). The injected tumor cells usually are altered to enhance their immunogenicity, such as by admixture with non-specific adjuvants, or by genetic modification of the cells to express cytokines, or other immune co-stimulatory molecules. The tumor cells employed can be autologous, i.e., derived from the same host as is being treated. Alternately, the tumor cells can be MHC-matched, or derived from another host having the same, or at least some of the same, MHC complex molecules.

Most whole cell cancer vaccines are produced using the patient's own tumor cells. There are two reasons for the use of such autologous vaccines. First, based on the results with murine tumors, it previously had been postulated that each tumor expresses tumor-associated-antigens (TAA) that are unique to each patient's tumor. Second, because T cell recognition depends on both the MHC allele as well as the specific antigen, use of cells from a patient's own tumor circumvents any need for matching of tumor or MHC antigens.

However, the in vitro expansion of fresh human tumor explants necessary for the production of autologous tumor cell vaccines is labor-intensive, technically demanding, and frequently impossible for most histologic types of human tumors, even with highly specialized research facilities. Moreover, the production of a vaccine from each patient's tumor is quite expensive. There also is a substantial likelihood that after extended passage of autologous cells in culture, the antigenic composition of such cells will change relative to the primary tumor from which the cell line originated, making the cells ineffective as a vaccine. While such change is frequent with all established cell lines, as regarding the use of autologous cells as a tumor vaccine, it potentially will require the maintenance of freezer stocks of each initially-isolated cell line for each patient being treated using this approach.

The recent results of Huang et al., Science, 264, 961–65 (1994), are relevant to the treatment of cancer using vaccines. Namely, prior to the study of Huang et al., tumor vaccine strategies were based on the understanding that the vaccinating tumor cells function as the antigen presenting cells (APCs) that present the tumor antigens on their MHC class I and II molecules, and directly activate the T cell arm of the immune response. In contrast, the results of Huang et al. indicate that the professional APCs of the host rather than the vaccinating tumor cells prime the T cell arm of the immune response. In the study of Huang et al., tumor vaccine cells secreting the cytokine GM-CSF recruit to the region of the tumor bone marrow-derived APCs. The bone marrow-derived-APCs take up the whole cellular protein of the tumor for processing, and then present the antigenic peptide(s) on their MHC class I and II molecules. In this fashion, the APCs prime both the $CD4^+$ and the $CD8^+$ T cell arms of the immune system, resulting in the generation of a systemic antitumor immune response that is specific for the antigenic epitopes of the host tumor. These results suggest that it may not be necessary to use autologous or MHC-matched tumor cells in cancer treatment.

Also relevant to the use of tumor vaccines, it has been confirmed that T cells are the critical mediator of systemic antitumor immunity induced by tumor vaccines (reviewed by Pardoll, Trends in Pharmacological Sciences, 14, 202–08 (1993)). Thus, the production of a universal tumor vaccine, i.e., a vaccine that is applicable to the majority of patients with a particular type of cancer, requires knowledge of the existence of shared immunodominant tumor antigens recognized by T cells. Currently, shared immunodominant tumor antigens recognized by T cells have been identified in only one human cancer, melanoma. Melanoma is a malignant neoplasm derived from cells that are capable of forming melanin, and may occur in the skin of any part of the body, in the eye, or, less commonly, in the mucous membranes of the genitalia, anus, oral cavity, or other sites. Melanomas frequently metastasize widely, and the regional lymph nodes, liver, lungs, and brain are likely to be involved. Primary malignant melanoma of the skin is the leading cause of death from all diseases arising in the skin. Metastatic melanoma is frequently thought of as resistant to treatment. In fact, the most effective single agent for treatment of disseminated melanoma, dacarbazine (dimethyltriazenoimidazolecarboxamide or DTIC), induces a partial remission in only 20 percent of cases, and a complete response in less than 5 percent of cases (Fitzpatrick et al., "Malignant Melanoma of the Skin", In Harrison's Principles of Internal Medicine, Braunwald et al., eds., Eleventh Ed. (McGraw-Hill Book Company: NY, 1987) 1595–97)).

The shared immunodominant melanoma antigens recognized by T cells fall into two main categories. One category of antigens encompasses proteins that are produced in melanoma cells, and are not produced in any other adult tissues with the exception of testis. These so-called tumor-specific shared antigens include the MAGE family antigens MAGE-1 and MAGE-3. Of these two antigens, MAGE-3 appears to be more widely produced and immunodominant than MAGE-1. MAGE-3 also is produced in other nonmelanotic tumors such as small cell lung cell carcinoma (SCLC), non-small cell lung cell carcinoma (non-SCLC), squamous cell carcinoma of the head and neck (SCCHN), colon cancer, and breast cancer. Similarly, MAGE-1 also is produced in breast cancer, glioblastoma, neuroblastoma, SCLC, and medullary cancer of the thyroid. The other category of shared melanoma antigens encompasses melanocyte lineage-specific differentiation antigens. These lineage-specific differentiation antigens are produced in melanocytes and their malignant counterpart, melanoma, and are produced in no other cells or tissues identified to date. These differentiation antigens include MART-1/Melan-A, tyrosinase, GP75, and GP100. These melanoma antigens, as well as other antigens (e.g., recently identified tumor-specific mutated antigens that may or may not prove to be shared), are further described in Table 1. It also is likely that further shared immunodominant melanoma antigens will be identified.

Table 1. Melanoma Antigens Recognized by T Cells

I. Melanocyte lineage-specific differentiation antigens
   gp100
   MART-1/Melan-A
   TRP1 (gp75)
   tyrosinase
II. Tumor-specific shared antigens
   MAGE-1
   MAGE-3
   BAGE
   GAGE-1,2
   GnT-V
   p15
III. Tumor-specific mutated antigens
   b-catenin
   MUM-1
   CDK4

Knowledge of these shared melanoma antigens would provide the potential to identify either a single melanoma cell line that expresses all, or a majority of, the shared melanoma antigens, or a set of melanoma cell lines which collectively express all, or a majority of, these antigens. If such melanoma cell lines could be identified, these cell lines when employed as a vaccine would share at least one, and in most cases would share multiple, antigens with melanomas from virtually every patient with melanoma. The present invention provides a method of treating cancer using such cell lines, and, in particular, provides a method of treating melanoma, which does not rely on use of autologous or MHC-matched tumor cells, and that avoids the difficulties and shortcomings associated with such use. These and other objects and advantages of the present invention, as well as additional inventive features, will be apparent from the description of the invention set forth herein.

BRIEF SUMMARY OF THE INVENTION

The present invention provides a method of treating or protecting against melanoma that comprises the steps of obtaining a melanoma cell line that expresses one or more shared immunodominant melanoma antigens, modifying the melanoma cell line to render it capable of producing an increased level of a cytokine relative to the unmodified cell line, and administering the melanoma cell line to a mammalian host that has melanoma or is at risk for developing melanoma. Preferably the melanoma cell line is allogeneic and is not necessarily MHC-matched to the host.

DESCRIPTION OF THE PREFERRED EMBODIMENTS

The method of the present invention of treating or protecting against melanoma comprises the steps of (a) obtaining a melanoma cell line that expresses one or more shared immunodominant melanoma antigens, (b) modifying the melanoma cell line to render it capable of producing an increased level of a cytokine relative to the unmodified melanoma cell line, and (c) administering the melanoma cell line to a mammalian host that has melanoma or is at risk for developing melanoma. Preferably, the administered melanoma cell line is allogeneic and is not necessarily MHC-matched to the host.

Melanoma

The method of the invention can be employed to treat or protect against melanoma. "Treating melanoma" according to the invention comprises administering to a host the melanoma cell lines set forth herein for the purpose of effecting a therapeutic response. Such treatment can be done in conjunction with other means for treatment of melanoma (e.g., surgical excision of a primary lesion). In particular, a therapeutic response is a systemic immune response (e.g., a T cell response) to melanoma antigens as further described herein. Such a response can be assessed by monitoring the attenuation of melanoma growth and/or melanoma regression. "Melanoma growth" includes an increase in melanoma size and/or the number of melanomas. "Melanoma regression" includes a reduction in melanoma mass. "Protecting against melanoma" according to the invention comprises administering to a susceptible host (e.g., hosts with poor tolerance to sunlight, patients with dysplastic nevi or large congenital melanocytic nevi, patients who have undergone resection of a primary melanoma lesion, etc.) the melanoma cell lines set forth herein for the purpose of preventing new melanoma from forming.

"Melanoma" according to the invention includes malignant tumors arising from melanocytes in the skin or other sites, and which may contain dark pigment. The term encompasses such cancers as are localized in primary tumors, as well as melanoma cells not localized in tumors, for instance, which expand from a tumor locally by invasion of adjacent tissue, or which have metastasized.

The method of treating or protecting against melanoma can be effectively carried out using a wide variety of different hosts. For instance, the method can be employed with various animalian hosts, but preferably is employed with mammalian hosts including, but not limited to, rodent, ape, chimpanzee, feline, canine, ungulate (such as ruminant or swine), as well as, in particular, human, hosts.

Melanoma Cell Line

As described herein, a "melanoma cell line" comprises cells that initially were derived from a melanoma. A melanoma cell line can be derived from any melanoma. Such cells typically have undergone some change such that they theoretically have indefinite growth in culture, i.e., unlike noncancerous cells, which can be cultured only for a finite period of time.

A melanoma cell line employed in a method of treating cancer can be obtained by any suitable means but preferably is obtained by a method comprising the steps of (a) obtaining a sample of a melanoma from a mammalian host, (b) forming a single cell suspension from the melanoma sample, (c) pelleting the melanoma cells, (d) transferring the melanoma cells into tissue culture using standard sterile culture technique, and (e) maintaining the melanoma cells in tissue culture under conditions that allow the growth of the melanoma cells, as further described herein.

More specifically, the sample of a melanoma typically is obtained at the time of surgery. The melanoma sample subsequently is handled and manipulated using sterile techniques, and in such a fashion so as to minimize tissue damage. The tissue sample preferably is placed on ice in a sterile container and moved to a laboratory laminar flow hood. The portion of the melanoma to be employed for isolation of a melanoma cell line is excised from the sample, and the remainder of the melanoma preferably is stored at a suitable temperature, e.g., $-70°$ C.

With use of a single cell suspension, the suspension is formed by enzymatically digesting the cells, preferably overnight. For instance, the sample is suspended in a solution that contains collagenase. The solution also can contain DNAse and/or hyaluronidase. Cell culture medium can be employed to carry out the digestion. The resultant single cell suspension is pelleted, and the pellets are resuspended in a small volume of tissue culture medium. The resuspended cells preferably then are inoculated into tissue culture medium appropriate for the growth of the cells in culture at a density of about $5 \times 10^5$ tumor cells/ml.

Alternately, the fresh tumor sample is minced into small pieces which are placed into culture directly. This other preferred method of isolating a melanoma cell line comprises the steps of (a) obtaining a sample of melanoma from a mammalian host, (b) mincing the sample to obtain fragments thereof, (c) transferring the fragments of fresh tumor into tissue culture, and (d) maintaining the melanoma cells in tissue culture under conditions that allow the growth of the cells.

Regardless of the means used to transfer the melanoma cells into tissue culture (and any means can be employed, such as is known to one of ordinary skill in the art), once transferred, the cultures can be maintained at about 35–40° C. in the presence of about 5–8% $CO_2$. Preferably the medium employed for cell growth is one that has wide applicability for supporting growth of many types of cell culture, e.g., a medium that utilizes a bicarbonate buffering system and various amino acids and vitamins. Optimally the medium is RPMI 1640 medium, which desirably has been supplemented with bovine serum (e.g., fetal bovine serum), preferably at a concentration of from about 5 to about 20%.

The medium can contain various additional factors as necessary, e.g., when required for the growth of the melanoma cells, or for maintenance of the melanoma cells in an undifferentiated state. The medium and medium components are readily available, and can be obtained, for instance, from commercial suppliers. The tumor cell cultures can be fed and recultured as necessary, e.g., typically every 1 to 10 days. The tumor cells also can be subjected to differential trypsinization to remove other cells (e.g., stromal cells) that can overgrow the primary tumor cultures. Also, suppression of fibroblast overgrowth can be achieved by supplementing the culture medium with cholera toxin (e.g., 10 ng/ml).

When it appears that a substantially purified culture of the melanoma cells has been obtained (e.g., as judged by the appearance or growth behavior of the cultures), various tests can be carried out as necessary or desirable to confirm the purity of the cultures. For instance, this can be confirmed by flow cytometry or immunocytology to validate expression of melanoma-associated proteins or gangliosides. This is done using antibodies that are readily available, and as known to one of skill in the art.

Shared Immunodominant Melanoma Antigens

Tests can be carried out on cells of the melanoma cell line to confirm that the melanoma cell line produces (i.e., "expresses") shared immunodominant antigens. Preferably according to the invention the melanoma cell line expresses one or more shared immunodominant melanoma antigens as described herein, or as identified in the future. The term "shared" refers to the fact that antigens unique to a particular individual's own tumor will not be useful for a generally applicable vaccine; rather, antigens that are shared by multiple (i.e., more than one) cases of a particular tumor type are required. The term "immunodominant" refers to the fact that for reasons of processing, binding to MHC or otherwise, certain antigens are capable of being more efficiently recognized by T cells from the vaccinated host.

In particular, preferably according to the invention, it is confirmed that tumor infiltrating lymphocytes from more than one patient, and, optimally, more than three patients, recognize the melanoma cell line. Moreover, RNA expression and/or protein production of shared immunodominant melanoma antigens desirably are assessed using standard techniques that are known in the art and are further described herein (e.g., PCR-based assays, Northern and Western assays, other immunological assays, and the like).

According to the invention, preferably the shared immunodominant melanoma antigens are selected from the group consisting of melanocyte-specific differentiation antigens and tumor-specific shared antigens, as defined herein, or which are identified at some point in the future. In particular, desirably the shared immunodominant melanoma antigens comprise one or more melanocyte-specific differentiation antigens and one or more tumor-specific shared antigens. Optimally the melanoma cell line expresses at least three shared immunodominant melanoma antigens. In a preferred embodiment, the shared immunodominant melanoma antigens are selected from the group consisting of MAGE-1, MAGE-3, MART-1/Melan-A, tyrosinase, gp75, gp100, BAGE, GAGE-1, GAGE-2, GnT-V, and p15 antigens.

The melanoma cell lines also can comprise tumor-specific mutated antigens. For instance, the melanoma cell lines preferably can comprise the b-catenin tumor-specific mutated antigen. Similarly, the melanoma cell lines preferably can comprise the MUM-1 tumor-specific mutated antigen. Also, the melanoma cell lines can comprise the CDK4 tumor-specific mutated antigen.

Preferably the melanoma cell line employed as a vaccine in the method of the invention exhibits stable production of shared immunodominant melanoma antigens with continued passage. In particular, preferably the melanoma cell line expresses the MAGE-3 antigen along with another shared immunodominant melanoma antigen. Desirably the melanoma cell line expresses two shared immunodominant antigens selected from the group consisting of the MAGE-3, tyrosinase, MART-1/Melan-A, gp75, and gp100 antigens. Even more preferably, the melanoma cell line expresses three shared immunodominant antigens selected from the group consisting of the MAGE-3, tyrosinase, MART-1/ Melan-A, gp75, and gp 100 antigens. Desirably, the melanoma cell line expresses four shared immunodominant antigens selected from the group consisting of the MAGE-3, tyrosinase, MART-1/Melan-A, gp75, and gp100 antigens. Optimally,the melanomacell line expresses the MAGE-3, tyrosinase, MART-1/Melan-A, gp75, and gp100 antigens. In particular, the melanoma cell line applied in the method of the invention preferably is 526-MEL or 624-MEL.

Cytokine

In the present inventive method of treating cancer, preferably the melanoma cell line has been modified to render it capable of producing an increased level of a cytokine relative to the unmodified melanoma cell line. A "cytokine" is, as that term is understood by one skilled in the art, any immunomodulating protein (including a modified protein such as a glycoprotein) that enhances the responsiveness of a host immune system to a melanoma present in the host. Preferably the cytokine is not itself immunogenic to the host, and potentiates immunity by activating or enhancing the activity of cells of the immune system.

As used herein, a cytokine includes, but is not restricted to, such proteins as interferons, interleukins (e.g., IL-1 to IL-17), tumor necrosis factor (TNF), erythropoietin (EPO), macrophage colony stimulating factor (M-CSF), granulocyte colony stimulating factor (G-CSF) and granulocyte-macrophagecolony stimulating factor (GM-CSF). Preferably the cytokine is GM-CSF.

"Modifying" a melanoma cell line according to the invention comprises the transfer of genetic material capable of imparting increased expression of a cytokine of interest. The genetic material can be in the form of naked DNA or a "vector" encompassing a DNA molecule such as a plasmid, virus or other vehicle, which contains one or more heterologous or recombinant DNA sequences, e.g., a cytokine gene or cytokine coding sequence of interest under the control of a functional promoter and possibly also an enhancer, and that is capable of functioning as a vector as that term is understood by those of ordinary skill in the art. Appropriate viral vectors include, but are not limited to simian virus 40, bovine papilloma virus, Epstein-Barr virus, adenovirus, herpes virus, vaccinia virus, Moloney murine leukemia virus, Harvey murine sarcoma virus, and Rous sarcoma virus.

Reference to a vector or other DNA sequences as "recombinant" merely acknowledges the linkage of DNA sequences which typically are not conjoined as isolated from nature. A "gene" is any nucleic acid sequence coding for a protein or a nascent mRNA molecule. Whereas a gene comprises coding sequences plus any non-coding (e.g., regulatory sequences), a "coding sequence" does not include any non-coding DNA. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription also is termed a "silencer". Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

Any suitable vector can be employed that is appropriate for introduction of nucleic acids into eukaryotic melanoma cells, or more particularly animal melanoma cells, such as mammalian, e.g., human, melanoma cells. Preferably the vector is compatible with the melanoma cell, e.g., is capable of imparting expression of the cytokine gene or coding sequence, and is stably maintained or relatively stably maintained in the melanoma cell. Desirably the vector comprises an origin of replication. Preferably the vector also comprises a so-called "marker" function by which the vector can be identified and selected (e.g., an antibiotic resistance gene). When a cytokine coding sequence (as opposed to a cytokine gene having its own promoter) is transferred, optimally the vector also contains a promoter that is capable of driving expression of the coding sequence and that is operably linked to the coding sequence. A coding sequence is "operably linked" to a promoter (e.g., when both the coding sequence and the promoter together constitute a native or recombinant cytokine gene) when the promoter is capable of directing transcription of the coding sequence.

As used herein, cytokine "gene" or "coding sequence" includes cytokine genomic or cDNA sequences, greater and lesser sequences and mutations thereof, whether isolated from nature or synthesized in whole or in part, as long as the gene or coding sequence is capable of expressing or capable of being expressed into a protein having the characteristic function of the cytokine, i.e., the ability to stimulate the host immune response. The means of modifying genes or coding sequences are well known in the art, and also can be accomplished by means of commercially available kits (e.g., New England Biolabs, Inc., Beverly, Mass.; Clontech, Palo Alto, Calif.). The cytokine gene or coding sequence can be of any suitable source, for example, isolated from any mammalian species such as human. Preferably, however, the cytokine gene or coding sequence comprises a GM-CSF sequence, particularly a human or murine GM-CSF gene or coding sequence including a human or murine GM-CSF cDNA sequence (e.g., as described by Cantrell et al., *Proc. Natl. Acad. Sci.*, 82, 6250–54 (1985)).

In the recombinant vectors of the present invention, preferably all the proper transcription, translation and processing signals (e.g., splicing and polyadenylation signals) are correctly arranged on the vector such that the cytokine gene or coding sequence will be appropriately transcribed and translated in the melanoma cells into which it is introduced. The manipulation of such signals to ensure appropriate expression in host cells is well within the knowledge and expertise of the ordinary skilled artisan. Whereas a cytokine gene is controlled by (i.e., operably linked to) its own promoter, another promoter, including a constitutive promoter, such as, for instance the adenoviral type 2 (Ad2) or type 5 (Ad5) major late promoter (MLP) and tripartite leader, the cytomegalovirus (CMV) immediate early promoter/enhancer, the Rous sarcoma virus long terminal repeat (RSV-LTR), and others, can be employed to command expression of the cytokine coding sequence.

Alternately, a tissue-specific promoter (i.e., a promoter that is preferentially activated in a given tissue and results in expression of a gene product in the tissue where activated) can be used in the vector. Such promoters include but are not limited to the elastase I gene control region which is active in pancreatic acinar cells as described by Swift et al., *Cell*, 38, 639–46 (1984) and MacDonald, *Hepatology*, 7, 425–515

(1987); the insulin gene control region which is active in pancreatic beta cells as described by Hanahan, *Nature*, 315, 115–22 (1985); the hepatocyte-specific promoter for albumin or alpha-1 antitrypsin described by Frain et al., *Mol. Cell. Biol.*, 10, 991–99 (1990) and Ciliberto et al., *Cell*, 41, 531–40 (1985); and the albumin and alpha-1 antitrypsin gene control regions which both are active in liver as described by Pinkert et al., *Genes and Devel.*, 1, 268–76 (1987) and Kelsey et al., *Genes and Devel.*, 1, 161–71 (1987).

Similarly, a melanoma-specificpromoter, akin to the carcinoembryonic antigen for colon carcinoma described by Schrewe et al., *Mol. Cell Biol.*, 10, 2738–48 (1990), can be used in the vector. Along the same cell lines, promoters that are selectively activated at different developmental stages (e.g., globin genes are differentially transcribed in embryos and adults) can be employed for gene therapy of certain types of cancer.

Another option is to use an inducible promoter, such as the IL-8 promoter, which is responsive to TNF, or the 6-16 promoter, which is responsive to interferons, or to use other similar promoters responsive to other cytokines or other factors present in a host or that can be administered exogenously. Use of a cytokine-inducible promoter has the added advantage of allowing for auto-inducible expression of a cytokine gene. According to the invention, any promoter can be altered by mutagenesis, so long as it has the desired binding capability and promoter strength.

Accordingly, the present invention provides a vector that comprises a nucleic acid sequence encoding a cytokine as defined above, and that can be employed in the method of the present invention of treating cancer. In particular, the present invention provides a recombinant vector comprising a nucleic acid sequence encoding a human GM-CSF. Thus, preferably, the present invention provides the vector designated as pcDNA3/Neo-GM-CSF, which is further described herein.

In the method of the present invention, the naked DNA or recombinant vector can be employed to transfer a cytokine gene or coding sequence to a cell in vitro, which preferably is a cell of an established melanoma cell line. Various methods can be employed for delivering new genetic material to cells in vitro. For instance, such methods include electroporation, membrane fusion with liposomes, high velocity bombardment with DNA-coated microprojectiles, incubation with calcium phosphate-DNA precipitate, DEAE dextran mediated transfection, infection with modified viral nucleic acids, direct microinjection into single cells, and the like. Other methods are available and are known to those skilled in the art. Thus, the present invention provides a substantially purified melanoma cell line wherein the cell line has been modified to render it capable of producing an increased level of a cytokine (preferably GM-CSF) relative to the unmodified melanoma cell line.

The level of cytokine produced by the modified melanoma cell is important in the context of the present invention for the purpose of obtaining an immunostimulatory response. Preferably the modified (e.g., transfected or transformed) melanoma cell line produces a level of cytokine that is increased over that observed for the unmodified (i.e., parental) melanoma cell line. Even more preferably, the modified cell line produces a level of cytokine that results in cytokine secretion greater than 36 ng/$10^6$ cells/day.

The present invention also encompasses a method of treating or protecting against melanoma wherein the cytokine is provided not by the administered melanoma cells, but is provided by some other means. This method comprises simply (a) obtaining a melanoma cell line that expresses one or more shared immunodominant melanoma antigens, and (b) administering the melanoma cell line to a mammalian host that has melanoma or is at risk for developing melanoma. In this method, the melanoma cell line is not modified prior to administration to render it capable of producing an increased level of a cytokine. Instead, cytokine is provided by some other means known in the art. For instance, cells of the melanoma cell line can be administered with cytokine encapsulated in microspheres (see, e.g., Golumbek et al., *Cancer Research*, 53, 1–4 (1993)) or liposomes (see, e.g., Nabel et al., *Proc. Natl. Acad. Sci.*, 90, 11307–11 (1993)).

Administering the Melanoma Cell Line

"Administering" cells of the melanoma cell line to a mammalian host refers to the actual physical introduction of the melanoma cells, particularly the modified (i.e., cytokine-producing) melanoma cells, into the host. Any and all methods of introducing the melanoma cells into the host are contemplated according to the invention; the method is not dependent on any particular means of introduction and is not to be so construed. Means of introduction are well known to those skilled in the art, and several such introduction means are exemplified herein.

While it is anticipated that the administered melanoma cell line may have some MHC antigens in common with the host melanoma, for the purpose of this invention, it is not necessary that the administered melanoma cell and the host have any MHC antigens in common. Accordingly, the present invention encompasses the administration of a melanoma cell line which is allogeneic (i.e., from a different individual) to the host, and which is not necessarily MHC-matched to the host. According to this invention a melanoma cell line is "not MHC-matched" to a host when it does not share any MHC antigens in common with the host, or when it does not share any of the MHC antigens with the host which typically are MHC-matched when using allogeneic melanoma cell vaccines (e.g., MHC class I antigens, especially HLA-A2).

Also, preferably the melanoma cell line (e.g., the modified melanoma cell line) is irradiated prior to administration to prevent cell replication, and possible melanoma formation in vivo. For irradiation of melanoma cells, the melanoma cells typically are harvested, transferred to a test tube in liquid medium, and irradiated at room temperature using a $^{137}CS$ source. Preferably the cells are irradiated at a dose rate of from about 50 to about 200 rads/min, even more preferably, from about 120 to about 140 rads/min. Preferably the cells are irradiated with a total dose sufficient to inhibit the majority of cells, preferably about 100% of the cells, from proliferating in vitro. Thus, desirably the cells are irradiated with a total dose of from about 10,000 to 30,000 rads.

Moreover, the melanoma cell line (e.g., the modified melanoma cell line) optimally is treated prior to administration to enhance its immunogenicity. Preferably this treatment comprises, as described herein, further genetic manipulation, such as, for instance, introduction of other cytokine or immune co-stimulatory functions, or, for example, admixture with nonspecific adjuvants including but not limited to Freund's complete or incomplete adjuvant, emulsions comprised of bacterial and mycobacterial cell wall components, and the like.

Accordingly, the allogeneic melanoma cell lines can be used to vaccinate patients with melanomas for the purpose of generating a systemic antimelanoma immune response against the patient's own melanoma. To the extent that MAGE-3 also is produced in other nonmelanotic tumors such as SCLC, non-SCLC, SCCHN, colon cancer, and breast cancer, and that MAGE-1 also is produced in breast cancer, glioblastoma, neuroblastoma, SCLC, and medullary cancer of the thyroid, allogeneic melanoma cell lines according to the invention that express MAGE-3 and/orMAGE-1 antigens also can be employed for the treatment of these other nonmelanotic tumors.

To facilitate administration, an allogeneic melanoma cell line according to the invention, particularly a modified allogeneic melanoma cell line that has been treated prior to administration to enhance its immunogenicity, can be made into a pharmaceutical composition or implant appropriate for administration in vivo, with appropriate carriers or diluents, which further can be pharmaceutically acceptable. The means of making such a composition or an implant have been described in the art (see, for instance, *Remington's Pharmaceutical Sciences,* 16th Ed., Mack, ed. (1980)). Where appropriate, a melanoma cell line can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Preferably, however, a pharmaceutically acceptable form is employed which does not ineffectuate the compositions of the present invention. Thus, desirably the melanoma cell line can be made into a pharmaceutical composition comprising a balanced salt solution, preferably Hanks' balanced salt solution, or normal saline.

Thus, the present invention provides a pharmaceutical composition that comprises a pharmaceutically acceptable carrier and cells of a melanoma cell line according to the invention, or any other melanoma cell line expressing one or more shared immunodominant antigens, as described herein. Preferably, the invention provides a pharma-ceutical composition comprising a pharmaceutically acceptable carrier and a melanoma cell line, particularly wherein the melanoma cell line is 526-MEL or 624-MEL, which has been modified to produce an increased level of a cytokine, optimally GM-CSF. The invention also provides a pharmaceutical composition that preferably comprises a pharmaceutically acceptable carrier and cells of a multiplicity of the melanoma cell lines according to the invention. For instance, the composition preferably comprises cells of more than one cell line according to the invention, and optimally comprises cells of more than one cell line, e.g., comprises 526-MEL and 624-MEL cells, or comprises cells selected from the group consisting of 526-MEL, 624-MEL, and some other cell line.

In pharmaceutical dosage form, a composition can be used alone or in appropriate association, as well as in combination, with other pharmaceutically active compounds and methods of treatment. For example, in applying a method of the present invention for the treatment of cancer, in particular, for the treatment of melanoma, such treatment can be employed in conjunction with other means of treatment of cancer, particularly melanoma, e.g., surgical ablation, irradiation, chemotherapy, and the like. In terms of chemotherapy, a composition according to the invention can be employed in addition to the use of dacarbazine, dactinomycin, carmustine, procarbazine, vinblastine, and interferon, as well as other drugs used to treat melanoma.

A pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration. Preferably delivery is accomplished by subcutaneous or intradermal administration.

A composition of the present invention can be provided in unit dosage form wherein each dosage unit, e.g., an injection, contains a predetermined amount of the composition, alone or in appropriate combination with other active agents. The term "unit dosage form" as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular host.

Preferably a sufficient number of the modified melanoma cells are present in the composition and introduced into the host such that expression of cytokine by the host cell, and subsequent recruitment of APCs to the melanoma site, results in a greater immune response to the extant host melanoma than would otherwise result in the absence of such treatment, as further discussed herein. Accordingly, the amount of vaccine cells administered should take into account the route of administration and should be such that a sufficient number of the melanoma cells will be introduced so as to achieve the desired therapeutic (i.e. immunopotentiating)response. Furthermore, the amounts of each active agent included in the compositions described herein (e.g., the amount per each cell to be contacted or the amount per certain body weight) can vary in different applications. In general, the concentration of modified melanoma cells preferably should be sufficient to provide in the host being treated at least from about $1 \times 10^6$ to about $1 \times 10^9$ melanoma cells, even more preferably, from about $1 \times 10^7$ to about $5 \times 10^8$ melanoma cells, although any suitable amount can be utilized either above, e.g., greater than $5 \times 10^8$ cells, or below, e.g., less than $1 \times 10^7$ cells.

These values provide general guidance of the range of each component to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation. Moreover, the effective amount of the compositions can be further approximated through analogy to other compounds known to inhibit the growth of cancer cells, in particular, melanoma cells.

One skilled in the art also is aware of means to monitor a therapeutic (i.e., systemic immune) response upon administering a composition of the present invention. In particular, the therapeutic response can be assessed by monitoring attenuation of melanoma growth and/or melanoma regression. The attenuation of melanoma growth or melanoma regression in response to treatment can be monitored using several end-points known to those skilled in the art including, for instance, the number of melanomas, melanoma mass or size, or reduction/prevention of metastasis. These described methods by no means are all-inclusive, and further methods to suit the specific application will be apparent to the ordinary skilled artisan.

EXAMPLES

The following examples further illustrate the present invention but, of course, should not be construed as in any way limiting its scope.

Example 1

This example illustrates the method of obtaining and culturing the melanoma cell lines that express one or more shared immunodominant melanoma antigens.

Melanoma cell lines were established from surgical resection specimens. Standard means as previously described and as known to one of ordinary skill in the art were employed to isolate the cell lines (see, e.g., Freshney, *Culture of Animal Cells*, (3d Ed.) Wiley-Liss, Inc., NY (1993)). In particular, the tumors were dispersed into single cell suspensions by overnight enzymatic digestion with collagenase, DNAse and hyaluronidase, and were cultured in RPMI 1640 containing 10% fetal bovine serum (FBS). The cells were then propagated in culture using standard sterile tissue culture technique.

Example 2

This example describes a characterization of the melanoma cell lines that expresses one or more shared immunodominant melanoma antigens.

the best MHC antigens to use for these purposes is HLA-A2 since it is expressed in roughly 50% of Caucasian individuals.

Thus, fresh tumor suspensions were passed over Ficoll-Hypaque gradients (Lymphocyte Separation Medium, Organon Technical Corporation, Durham, N.C.) to isolate and grow T cell populations that recognize melanoma. The gradient interfaces containing viable tumor cells and lymphocytes were washed, adjusted to a total cell concentration of about 2.5 to about $5.0 \times 10^5$ cells per ml, and cultured in complete medium. Complete medium consisted of RPMI 1640 with 10% heat-inactivated type AB human serum, 50 IU/ml penicillin and 50 mg/ml streptomycin (Biofluids, Rockville, Md.), 50 mg/ml gentamicin (GIBCO Laboratories, Chagrin Falls, Ohio), 10 mM HEPES buffer (Biofluids), and 2 mM L-glutamine (MA Bioproducts, Walkersville, Md.). The medium was supplemented with 6000 IU/ml IL-2 and the supernatant from LAK cell cultures. Cultures were maintained at 37° C. in a 5% $CO_2$ humidified atmosphere in a variety of tissue culture vessels, including 24-well plates and 175 cm² flasks. Under these conditions, tumor-infiltrating T cells grow selectively. Tumor infiltrating lymphocyte (TIL) cultures were expanded in IL-2 for at least four weeks.

For analysis of TIL recognition of the melanoma cell lines (Topalian et al., *J. Immunol.* 142, 3714 (1989)), the cytolytic activity of cultured TIL against these cell lines was assessed using standard 4 hour $^{51}Cr$ release assays. Alternately, specific secretion of cytokines by TIL cocultured with tumor cells was monitored. The results of these experiments are presented in Table 2.

TABLE 2

LYSIS OF HLA-A2+ MELANOMAS BY HLA-A2-RESTRICTED MELANOMA TIL

| | Targets (% Lysis, E:T = 40) | | | | | | | | |
|---|---|---|---|---|---|---|---|---|---|
| Effectors | 526-MEL | 553-MEL | 624-MEL | 677-MEL | 697-MEL | 1102-MEL | 1011-MEL | 560-fibro | Daudi lymphoma |
| Exp. A | | | | | | | | | |
| TIL 620 | 48 | 35 | 55 | 67 | 53 | 33 | 5 | −1 | −1 |
| TIL 1073 | 40 | 26 | 44 | 29 | 24 | 23 | −1 | −3 | −6 |
| TIL 1143 | 33 | 41 | 54 | 54 | 34 | 29 | 0 | −2 | −5 |
| TIL 1235 | 24 | 15 | 34 | 37 | 27 | 8 | 0 | 0 | −4 |
| LAK Cells | 30 | 79 | 60 | 62 | 18 | 53 | 63 | 51 | 68 |
| Exp. B | | | | | | | | | |
| TIL 501 | 58 | 19 | 53 | 54 | 47 | 7 | 0 | 8 | −2 |
| TIL 660 | 47 | 26 | 50 | 46 | 41 | 6 | 1 | 0 | 1 |
| TIL 1074 | 13 | 9 | 14 | 8 | 5 | 2 | −2 | 0 | −3 |
| TIL 1128 | 17 | 4 | 20 | 15 | 18 | 3 | 0 | 0 | −2 |
| LAK Cells | 53 | 77 | 55 | 72 | 38 | 52 | 62 | 69 | 63 |
| HLA-A2 | + | + | + | + | + | + | − | + | − |

The presence within a melanoma cell line of shared immunodominant antigens can be confirmed by showing that T cells from patients with melanoma that recognize the patient's own melanoma also will recognize the particular allogeneic melanoma cell line in question. In order to make this determination, there must be sharing of at least one MHC class I antigen between the patient from which the T cells are derived and the melanoma line being tested. One of As shown in Table 2, TIL cultures from eight different HLA-A2+ patients (i.e., TIL 620, TIL 1073, TIL 1143, TIL 1235, TIL 501, TIL 660, TIL 1074, and TIL 1128) were tested against seven different established melanoma cell lines (i.e., 526-MEL, 553-MEL, 624-MEL, 677-MEL, 697-MEL, 11 02-MEL, and 1011-MEL) as well as an established fibroblast cell line (560-fibro) and the Daudi lymphoma cell line. Two of the tumor cell lines, i.e., 526-MEL and 624-

MEL, were recognized by all of the TIL cultures as determined by the specific lysis in a chromium release assay of >10% at an effect to target tumor cell ration (E:T) equal to 40. Other of the melanoma cell lines except for 1011-MEL (HLA-A2 negative) were recognized by the majority of, or at least one of, the TIL cultures.

526-MEL and 624-MEL were tested by reverse-transcriptasepolymerase chain reaction (RT-PCR) or Northern blotting for expression of the MZ2-E (or MAGE-1), MZ2-D (or MGE-3), MART-1/Melan-A, GP100, and GP75 antigens. The cell lines were assessed for tyrosinase production via recognition by a tyrosinase specific helper T cell line. The cell lines also were assessed for expression of GD3 by staining with a specific monoclonal antibody. The results of these experiments are presented in Table 3.

TABLE 3

EXPRESSION OF SHARED MELANOMA ANTIGENS BY MELANOMA CELL CULTURES

| Antigen | 526-MEL | 624-MEL |
| --- | --- | --- |
| MAGE-1 (MZ2-E) | − | − |
| MAGE-3 (MZ2-D) | + | + |
| Tyrosinase | + | + |
| MART-1/Melan-A | + | + |
| GP100 | + | + |
| GP75 | + | + |
| GD3 | + | + |

Both cell lines expressed all the common shared antigens tested by these assays with the exception of the MAGE-1 antigen, as presented in Table 3.

These results confirm that the 526-MEL and 624-MEL melanoma cell lines express the majority of the immunodominant shared melanoma antigens. The results further confirm that the methods described herein can be employed to obtain and/or identify a melanoma cell line that expresses one or more shared immunodominant melanoma antigens.

Example 3

This example illustrates the method of modifying a melanoma cell line that expresses one or more shared immunodominant melanoma antigens to produce an increased amount of a cytokine. The cytokine granulocyte-macrophagecolony stimulating factor (GM-CSF) is potentially more potent than other cytokines in generating a systemic antimelanoma response in preclinical melanoma models (see, e.g., Dranoff et al., *Proc. Natl. Acad. Sci.*, 90, 3539–42(1993)). Accordingly,the melanoma cell lines were modified to secrete GM-CSF. The melanoma cell lines 526-MEL and 624-MEL described in Example 1 were employed as representative of an allogeneic melanoma cell line that expresses one or more shared immunodominant melanoma antigens.

To facilitate manipulation of the cell lines, a recombinant human GM-CSF gene was cloned into pcDNA3/Neo (Invitrogen). The resulting recombinant vector is henceforth designated pcDNA3/Neo-GM-CSF. All cloning reactions and DNA manipulations were carried out using methods that are well known to the ordinary skilled artisan, and which have been described in the art (see, e.g., Maniatis et al., *Molecular Cloning: A Laboratory Manual*, 2nd ed. (Cold Spring Harbor Laboratory, NY, (1982))). Enzymes employed in these reactions were obtained from commercial suppliers (e.g., New England Biolabs, Inc., Beverly, Mass.; Clontech, Palo Alto, Calif.; Boehringer Mannheim, Inc., Indianapolis, Ind.; etc.), and were used according to the manufacturers' recommendations.

The plasmid pcDNA3/Neo-GM-CSF contains the human GM-CSF cytokine coding sequence under the control of the cytomegalovirus (CMV) promoter, and also contains the neomycin resistance gene controlled by a separate CMV promoter. The CMV promoter was employed since it is able to drive a relatively high level of gene expression in most eukaryotic cells (Boshart et al., *Cell*, 41, 521–30 (1985)). Initial studies using this vector for gene transfer to a human melanoma cell line confirm that, following selection for neomycin resistance, secreted levels of GM-CSF greater than 36 ng/$10^6$ cells/day were achieved. These initial studies confirm that the pcDNA3/Neo-GM-CSF plasmid is functional in eukaryotic cells. Moreover, this is the dose of GM-CSF that is required to generate an adequate antimelanoma immune response in a mouse model. Dilution experiments using varying concentrations of melanoma cells that either were or were not transduced with a retroviral vector carrying a GM-CSF gene confirm that, in the B16-F10 melanoma system, GM-CSF secretion below 36 ng/$10^6$ cells/day fails to generate the potent antimelanoma immunity seen at levels of secretion above this threshold. These findings underscore the importance of delivering high and sustained levels of GM-CSF directly at the site of the vaccinating melanoma cells that are the source of the relevant melanoma antigen.

The 526-MEL and 624-MEL cell lines were transfected with pcDNA3/Neo-GM-CSF by the calcium phosphate procedure. For these experiments, 526-MEL was transfected at culture passage 32, and 624-MEL was transfected at culture passage 28. GM-CSF levels were determined by ELISA. The results of these experiments are presented in Table 4.

TABLE 4

GM-CSF SECRETION BY TRANSFECTED MELANOMA CELL LINES

| Cell Line | Passage # | GM-CSF (ng/$10^6$ melanoma cells/day) |
| --- | --- | --- |
| 526-MEL | 40 | 4.9 |
|  | 43 | 2.1 |
|  | 44 | 8.2 |
| 624-MEL | 35 | 18.4 |
|  | 37 | 37.0 |
|  | 38 | 85.5 |

The GM-CSF secretion level observed for the 526-MEL cell line was less than 10 ng/$10^6$ melanoma cells/day. It is possible that GM-CSF secretion for the 526-MEL cell line can be increased with use of a different expression vector for transfection, or by selecting melanoma cell lines with higher levels of expression. In comparison, the GM-CSF secretion level observed for the melanoma cell line 624-MEL was over 80 ng/$10^6$ melanoma cells/day. Nontransfected melanomas did not secrete measurable amounts of GM-CSF.

The methods employed in this example also can be used to generate melanoma cell lines capable of producing increased amounts of other cytokines, and can be used with other melanoma cell lines, all of which similarly can be employed as vaccines.

Example 4

This example illustrates further studies regarding GM-CSF administration to a host.

Further studies confirm that GM-CSF secretion needs to parallel the known paracrine physiology of this cytokine. In particular, secretion must be at the site of the relevant antigens (i.e., the melanoma cells), as described in the previous example, and high levels must be sustained for several days (see, e.g., Dranoff et al., supra; Golumbek et al., supra). However, it appears that the melanoma cell itself need not be the source of GM-CSF secretion (Golumbek et al., supra). Immunologic protection and histologic infiltrates similar to those seen with retrovirally-transduced cytokine-expressing melanoma cells can be generated when GM-CSF is slowly released from biodegradable polymers co-injected with the melanoma cell. In addition, if a second non-cross reacting tumor is co-injected with a GM-CSF secreting melanoma, immunologic protection against both tumors can be generated. Simple injection of soluble GM-CSF along with melanoma cells, however, does not provide sustained local levels of this cytokine and does not generate systemic immunity (Golumbek et al., supra). Thus, the effectiveness of using an allogeneic melanoma cell that was not MHC-matched to the host cell for delivery of cytokine in vivo was explored.

In murine models, it was demonstrated that the antimelanoma immunity generated with the delivery of GM-CSF by bystander allogeneic melanoma cells is comparable to that achieved when GM-CSF is delivered by the target melanoma cell itself. Specifically, in these experiments, BALB/c mice were subcutaneously vaccinated with irradiated CT26 colon carcinoma cells, with GM-CSF delivered either by retrovirally-transduced CT26 cells, or by retrovirally-transducedallogeneic B16-F10 cells. Two weeks later, mice were rechallenged with injections of wild-type strain CT26. The CT26 colon carcinoma cell line possesses some intrinsic immunogenicity; however, a greater degree of protection was seen when GM-CSF was secreted at the vaccination site, whether by the syngeneic or the allogeneic cells. While it is unclear to what degree, or by what mechanism, the allogeneic melanoma cells can augment anti-CT26 immunity, these data strongly suggest that allogeneic delivery of GM-CSF in the context of the present invention is likely to be at least as effective as autologous melanoma delivery.

Example 5

This example illustrates the method of treating cancer by administering to a host in accordance with the invention, a melanoma cell line that expresses one or more shared immunodominant melanoma antigens, and preferably is allogeneic and is not necessarily MHC-matched to the host.

Melanoma cell lines that secrete GM-CSF, preferably at levels greater than 36 ng/$10^6$ melanoma cells/day, are obtained and employed. The modified melanoma cells are harvested from the tissue culture flasks by trypsinization. The cells are washed using normal saline, pelleted, and resuspended in Hanks' balanced salt solution, or some other salt solution appropriate for introduction in vivo. The cells are resuspended at a concentration of from about $1\times10^6$ to about $1\times10^8$ melanoma cells/ml. From about 0.1 to about 0.5 ml of this resuspension mixture is employed as a vaccine. Thus, preferably from about $1\times10^6$ to about $1\times10^9$ melanoma cells are injected, and, optimally, from about $1\times10^7$ to about $5\times10^8$ melanoma cells are injected in toto. Whereas the modified melanoma cells are injected subcutaneously in the mouse, the cells preferably are injected intradermally in humans.

Prior to injection, the modified melanoma cells can be irradiated, e.g., using a $^{137}Cs$ source. Such irradiation prevents the replication of the tumor cells, but allows the cells to secrete GM-CSF and to remain metabolically active for at least a week in culture. Preferably irradiation can be carried out using a $^{137}Cs$ source at a dose rate of about 120–140 rads/min to deliver a total dose of about 15,000 rads. The modified melanoma cells also can be altered to enhance their immunogenicity. For instance, the cells further can be genetically manipulated (e.g., through insertion of other cytokine or other immune stimulatory nucleic acid sequences, e.g., a cytokine other than, or in addition to GM-CSF ), or can be admixed with non-specific adjuvants (e.g., Freund's complete or incomplete adjuvant, emulsions comprised of bacterial and mycobacterial cell wall components, and the like).

The invention can be used in mammals (particularly humans) with melanoma, or that are at risk for developing melanoma. It also is anticipated that the patient can be treated prior to, or in addition to (i.e., concurrently or immediately following), immunotherapy as described herein with any number of methods as are employed to treat cancer, for instance, surgical resection, irradiation, chemotherapy, and the like.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A method of inducing a systemic immune response to shared melanoma antigens in a mammal having melanoma, comprising:
    (a) providing cells of at least one melanoma cell line that
        (i) express a plurality of shared melanoma antigens that are shared with the melanoma of said mammal;
        (ii) are transfected with a nucleic acid vector encoding a cytokine that recruits antigen presenting cells and enhances antigen presentation;
        (iii) are allogeneic to said mammal; and
        (iv) are irradiated prior to step (b);
    (b) administering an effective number of said cells to said mammal, which cells express said plurality of shared melanoma antigens and functionally express said cytokine,
thereby inducing a systemic immune response specific to said plurality of shared melanoma antigens.

2. The method of claim 1 wherein said administering of step (b) is subcutaneous, intradermal or intramuscular.

3. A method of inducing an antitumor response in a mammal having melanoma, comprising:
    (a) providing cells of at least one melanoma cell line that
        (i) express a plurality of shared melanoma antigens that are shared with the melanoma of said mammal;
        (ii) are transfected with a nucleic acid vector encoding a cytokine that recruits antigen presenting cells and enhances antigen presentation;
        (iii) are allogeneic to said mammal; and
        (iv) are irradiated prior to step (b);
    (b) administering an effective number of said cells to said mammal, which cells express said plurality of shared melanoma antigens and functionally express said cytokine
thereby inducing an antitumor response that is characterized by:

(A) at least a 50% decrease in the sum of the products of maximal perpendicular diameters of all measurable lesions;

(B) no evidence of new lesions, and (C) no progression of any preexisting lesions.

4. The method of claim 3 wherein said administering of step (b) is subcutaneous, intradermal or intramuscular.

5. A method of inducing regression or attenuation of growth of melanoma in a mammal having melanoma, comprising:

(a) providing cells of at least one melanoma cell line that
   (i) express a plurality of shared melanoma antigens that are shared with the melanoma of said mammal;
   (ii) are transfected with a nucleic acid vector encoding a cytokine that recruits antigen presenting cells and enhances antigen presentation;
   (iii) are allogeneic to said mammal; and
   (iv) are irradiated prior to step (b);

(b) administering an effective number of said cells to said mammal, which cells express said plurality of shared melanoma antigens and functionally express said cytokine, thereby inducing a systemic immune response specific to said plurality of shared melanoma antigens of said melanoma, and thereby inducing said regression or attenuation of growth of said melanoma.

6. The method of claim 5 wherein said administering of step (b) is subcutaneous, intradermal or intramuscular.

7. A method of inhibiting recurrent growth of a melanoma tumor in a mammal:

(a) providing cells of at least one melanoma cell line that
   (i) express a plurality of shared melanoma antigens that are shared with the melanoma of said mammal;
   (ii) are transfected with a nucleic acid vector encoding a cytokine that recruits antigen presenting cells and enhances antigen presentation;
   (iii) are allogeneic to said mammal; and
   (iv) are irradiated prior to step (b);

(b) administering an effective number of said cells to said mammal, which cells express said plurality of shared melanoma antigens and functionally express said cytokine, thereby inducing a systemic immune response specific to said plurality of shared melanoma antigens in said mammal, which immune response inhibits said recurrent growth of said melanoma tumor.

8. The method of claim 7 wherein said administering of step (b) is subcutaneous, intradermal or intramuscular.

9. The method of any of claims 1–8, wherein said melanoma cell line is MHC-mismatched with said mammal.

10. The method of any of claims 1–8, wherein said shared melanoma antigens are
   (a) melanocyte-specific differentiation antigens,
   (b) tumor-specific shared antigens,
   (c) a combination of (a) and (b).

11. The method of any of claims 1–8, wherein said melanoma cell line cells being administered express at least three shared melanoma antigens.

12. The method of any of claims 1–8, wherein said melanoma antigens expressed by said cells being administered are selected from the group consisting of MAGE-1, MAGE-3, MART-1/Melan-A, tyrosinase, gp75, gp100, BAGE, GAGE-1, GAGE-2, GnT-V, and p15.

13. The method of claim 12, wherein said melanoma antigens are selected from the group consisting of MAGE-3, tyrosinase, MART-1/Melan-A, gp75, and gp100.

14. The method of any of claims 1–8, wherein said melanoma cell line is selected from the group consisting of 526-MEL and 624-MEL.

15. The method of any of claims 1–8, wherein said cytokine is GM-CSF.

16. The method of any of claims 1–8, wherein said cells being administered are administered in combination with at least one cytokine and/or at least one adjuvant.

17. The method of claim 16, wherein said cytokine administered with said cells is GM-CSF.

* * * * *